United States Patent [19]
Audia et al.

[11] Patent Number: 6,107,307
[45] Date of Patent: Aug. 22, 2000

[54] INHIBITION OF SEROTONIN REUPTAKE

[75] Inventors: James Edmund Audia, Indianapolis; Stacey Leigh McDaniel, Martinsville; Jeffrey Scott Nissen, Indianapolis, all of Ind.

[73] Assignee: Eli Lilly and Company, Indianapolis, Ind.

[21] Appl. No.: 09/326,924

[22] Filed: Jun. 7, 1999

Related U.S. Application Data

[60] Provisional application No. 60/089,951, Jun. 19, 1998.
[51] Int. Cl.$^7$ .......................... A61K 31/44; C07D 401/00
[52] U.S. Cl. ............................................. 514/304; 546/126
[58] Field of Search .................................... 546/125, 126; 514/304

[56] References Cited

U.S. PATENT DOCUMENTS

| | | | |
|---|---|---|---|
| 2,902,490 | 9/1959 | Archer et al. | 260/292 |
| 4,959,367 | 9/1990 | King et al. | 514/243 |
| 5,234,931 | 8/1993 | Glamkowski et al. | 514/304 |
| 5,491,148 | 2/1996 | Berger et al. | 514/305 |

FOREIGN PATENT DOCUMENTS

| | | |
|---|---|---|
| WO 95/03048 | 2/1995 | WIPO . |
| WO 97/13770 | 4/1997 | WIPO . |
| WO 9716192 | 5/1997 | WIPO . |

OTHER PUBLICATIONS

Layer, et. al., Structurally modified ibogaine analogs exhibit differing affinities for NMDA receptors, European Journal of Pharmacology, 309, pp. 159–165, 1996.

Langlois, et. al., Synthesis of quinazoline–2,4–dione and naphthalimide derivatives as new 5–HT3 receptor antagonists, J. Med. Chem. 29, pp. 925–940, 1994.

Clark, et. al., "2–(Quinuclinin–3–yl)pyrido[4,3–b] indol–1–ones and Isoquinolin–1–ones. Potent Conformationally Restricted 5–HT3 Receptor Antagonists", Journal of Medicinal Chemistry, vol. 36, pp. 2645–2657, 1993.

Repke, et. al., Abbreviated Ibogaine Congeners. Synthesis and Reachtions of Tropan–3–yl–2– and –3–indoles. "Investigation of an Unusual Isomerization of 2–Substituted Indoles Using Computational and Spectroscopic Techniques", J. of Org. Chem., vol. 59, 1994.

King, et. al., Benzotriazinones as "Virtual Ring" Mimics of o–Methoxybenzamides: Novel and Potent 5–HT3 Receptor Antagonists, Journal of Medicinal Chemistry, vol. 33, No. 11, pp. 2942–2944.

Journal of Chemistry, 1975, 40, 2525–2529.

J. Med. Chem, 1995, 38, 379–388.

J. Med Chem, 1996, 39, 4027–2035.

*Primary Examiner*—Zinna Northington Davis
*Assistant Examiner*—Binta Robinson
*Attorney, Agent, or Firm*—Robert D. Titus

[57] ABSTRACT

This invention provides 3-(bicyclic heteroaryl)-8-azabicyclo [3.2.1]oct-2-enes and 3-(bicyclic heteroaryl)-8-azabicyclo [3.2.1]octanes which are useful for the inhibition of serotonin reuptake in mammals.

9 Claims, No Drawings

INHIBITION OF SEROTONIN REUPTAKE

PRIORITY INFORMATION

This application claims the benefit of U.S. Provisional Application 60/089,951 filed Jun. 19, 1998.

BACKGROUND OF THE INVENTION

During the past two decades, the relationship between neuronal monoamines in the brain and a variety of diseases and conditions has been appreciated and investigated. The discovery of selective monoamine reuptake inhibitors has provided the medical community with exciting new tools with the potential for treatment of several physiological and psychological disorders. Reuptake inhibitors increase the levels of endogenous monoamines by inhibiting the neuronal mechanism for recovering the monoamine from the synapse without interfering with the neuronal receptors. If the reuptake inhibitor is selective for a particular monoamine, undesirable side-effects from the therapy can be reduced.

Fluoxetine, a selective inhibitor of serotonin reuptake, has gained wide acceptance as a therapy for the treatment of depression and eating disorders, and is under active investigation for the treatment of other disorders. Similarly, tomoxetine hydrochloride [(−)-N-methyl-3-(2-methylphenoxy)propanamine hydrochloride] is a selective inhibitor of norepinephrine uptake being investigated clinically for the treatment of urinary incontinence. These compounds are among many taught in U.S. Pat. Nos. 4,018,895, 4,194,009, 4,314,081 and 5,026,707 as being potent inhibitors of the uptake of various physiologically active monoamines, including serotonin, norepinephrine and dopamine.

Certain 8-methyl-3-aryl-8-azabicyclo[3.2.1]-2-enes have been reported to possess useful monoamine neurotransmitter reuptake inhibition activity (WO 97/13770). The serotonin reuptake inhibition activity of 3-(bicyclic heteroaryl)-8-azabicyclo[3.2.1]-2-enes and 3-(bicyclic heteroaryl)-8-azabicyclo[3.2.1]-2-anes has heretofore not been appreciated.

SUMMARY OF THE INVENTION

The present invention provides the optionally substituted 3-(bicyclic heteroaryl)-8-azabicyclo[3.2.1]oct-2-enes and 3-(bicyclic heteroaryl)-8-azabicyclo[3.2.1]oct-anes of Formula I:

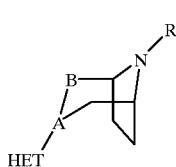

where
A-B is —C=CH— or —CH—CH$_2$—;
R is H, or C$_1$–C$_4$; and
HET is a bicyclic heteroaryl group optionally substituted with one or two substitutents independently selected from the group consisting of H, halo, C$_1$–C$_4$ alkyl, C$_3$–C$_6$ cycloalkyl, C$_1$–C$_4$ alkoxy, cyano, nitro, carboxamido, trifluoromethyl, or hydroxy; and pharmaceutically acceptable salts thereof.

The present invention also provides a method for the inhibition of serotonin reuptake comprising administering to a mammal in need of such inhibition a pharmaceutically effective amount of a compound of Formula I.

This invention furthermore provides a pharmaceutical formulation which comprises, in association with a pharmaceutically acceptable carrier, diluent or excipient, a compound of Formula I.

DETAILED DESCRIPTION

The general chemical terms used in the formulae above have their usual meanings. For example, the term "alkyl" includes such groups as methyl, ethyl, n-propyl, isopropyl, n-butyl, isobutyl, sec-butyl, tert-butyl, and the like. The term "alkoxy" includes methoxy, ethoxy, propoxy, isopropoxy, butoxy and the like. The term "C$_3$–C$_6$ cycloalkyl" includes cyclopropyl, cyclobutyl, cyclopentyl and cyclohexyl. The term "halo" includes fluoro, chloro, bromo and iodo.

The term "bicyclic heteroaryl" is taken to mean benzo-fused five- and six-membered heterocyclic rings containing one or two heteroatoms independently selected from nitrogen, sulfur and oxygen. The bicyclic heteroaryls contemplated by the present invention include: indol-2-yl, indol-3-yl, benzothien-2-yl, benzothien-3-yl, benzofur-2-yl, benzofur-3-yl, benzothiazol-2-yl, benzoxazol-2-yl, benzoisothiazol-3-yl, benzoisoxazol-3-yl, benzimidazol-2-yl, quinolin-2-yl, quinolin-3-yl, quinolin-4-yl, isoquinolin-1-yl, isoquinolin-3-yl, isoquinolin-4-yl, and quinoxalin-2-yl.

While all of the compounds of Formula I are useful for the inhibition of serotonin reuptake, certain classes of the compounds are preferred. The following paragraphs describe such preferred classes.

a) A-B is —C=CH—;
b) A-B is —CH—CH$_2$—;
c) R is hydrogen;
d) R is methyl;
e) HET is selected from indol-2-yl, indol-3-yl, benzofur-2-yl, benzofur-3-yl, benzothien-2-yl, and benzothien-3-yl;
f) HET is indol-3-yl;
g) HET is selected from quinolin-2-yl, quinolin-3-yl, and quinolin-4-yl;
h) HET is monosubstituted with halogen;
i) HET is monosubstituted with chloro;
j) HET is monosubstituted with trifluoromethyl;
k) HET is indol-2-yl, indol-3-yl, benzothien-2-yl, or benzothien-3-yl monosubstituted at the 6-position;
l) HET is indol-2-yl, indol-3-yl, benzothien-2-yl, or benzothien-3-y monosubstituted at the 7-position;
m) HET is disubstituted with halogen;
n) HET is indol-2-yl, indol-3-yl, benzothien-2-yl, or benzothien-3-yl disubstituted with halogen;
o) The compound is a salt;
p) The compound is a free base.

It will be understood that the above classes may be combined to form additional preferred classes.

Since the compounds of this invention are amines, they are basic in nature and accordingly react with any of a number of inorganic and organic acids to form pharmaceutically acceptable acid addition salts. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogen-phosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzo-ate, hydroxybenzoate, methoxybenzoate, phthalate, sulfon-ate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid.

The following group is illustrative of the compounds of the present invention:

3-(4-chlorobenzothien-2-yl)-8-methyl-8-azabicyclo-[3.2.1]octane hydrobromide 3-(4-nitrobenzothien-3-yl)-8-ethyl-8-azabicyclo-[3.2.1]octane maleate 3-(4-cyanoindol-2-yl)-8-propyl-8-azabicyclo-[3.2.1]octane oxalate 3-(4-carboxamidoindol-3-yl)-8-isopropyl-8-azabicyclo-[3.2.1]octane phosphate 3-(4-ethoxybenzofur-2-yl)-8-isopropyl-8-azabicyclo-[3.2.1]octane trifluoromethanesulfonate 3-(7-ethylbenzofur-3-yl)-8-butyl-8-azabicyclo-[3.2.1]octane p-toluenesulfonate 3-(5-fluorobenzothiazol-2-yl)-8-isobutyl-8-azabicyclo-[3.2.1]octane hydrobromide 3-(6-trifluoromethylbenzoxazol-2-yl)-8-sec-butyl-8-azabicyclo[3.2.1]octane maleate 3-(5-hydroxybenzoisothiazol-3-yl)-8-tert-butyl-8-azabicyclo[3.2.1]octane oxalate 3-(5-cyclopropylbenzoisoxazol-3-yl)-8-azabicyclo-[3.2.1]octane phosphate 3-(4,5-dichlorobenzoimidazol-2-yl)-8-methyl-8-azabicyclo[3.2.1]octane trifluoromethanesulfonate 3-(7-propoxy-5-ethylquinolin-2-yl)-8-methyl-8-azabicyclo[3.2.1]octane p-toluenesulfonate 3-(5,6-difluoroquinolin-3-yl)-8-methyl-8-azabicyclo-[3.2.1]octane 3-(5-methyl-7-chloroquinolin-4-yl)-8-methyl-8-azabicyclo[3.2.1]octane benzoate 3-(5-methoxy-6-fluoroisoquinolin-3-yl)-8-methyl-8-azabicyclo[3.2.1]octane 3-(6-cyclohexylisoquinolin-4-yl)-8-methyl-8-azabicyclo[3.2.1]octane hydrobromide 3-(6-hydroxyquinoxalin-2-yl)-8-methyl-8-azabicyclo-[3.2.1]octane maleate 3-(4-chlorobenzothien-2-yl)-8-methyl-8-azabicyclo-[3.2.1]oct-2-ene hydrobromide 3-(4-nitrobenzothien-3-yl)-8-ethyl-8-azabicyclo-[3.2.1]oct-2-ene maleate 3-(4-cyanoindol-2-yl)-8-propyl-8-azabicyclo-[3.2.1]oct-2-ene oxalate 3-(4-carboxamidoindol-3-yl)-8-isopropyl-8-azabicyclo-[3.2.1]oct-2-ene phosphate 3-(4-ethoxybenzofur-2-yl)-8-isopropyl-8-azabicyclo-[3.2.1]oct-2-ene trifluoromethanesulfonate 3-(7-ethylbenzofur-3-yl)-8-butyl-8-azabicyclo-[3.2.1]oct-2-ene p-toluenesulfonate 3-(5-fluorobenzothiazol-2-yl)-8-isobutyl-8-azabicyclo-[3.2.1]oct-2-ene hydrobromide 3-(6-trifluoromethylbenzoxazol-2-yl)-8-sec-butyl-8-azabicyclo[3.2.1]oct-2-ene maleate 3-(5-hydroxybenzoisothiazol-3-yl)-8-tert-butyl-8-azabicyclo[3.2.1]oct-2-ene oxalate 3-(5-cyclopropylbenzoisoxazol-3-yl)-8-azabicyclo-[3.2.1]oct-2-ene phosphate 3-(4,5-dichlorobenzoimidazol-2-yl)-8-methyl-8-azabicyclo[3.2.1]oct-2-ene trifluoromethanesulfonate 3-(7-propoxy-5-ethylquinolin-2-yl)-8-methyl-8-azabicyclo[3.2.1]oct-2-ene p-toluenesulfonate 3-(5,6-difluoroquinolin-3-yl)-8-methyl-8-azabicyclo-[3.2.1]oct-2-ene 3-(5-methyl-7-chloroquinolin-4-yl)-8-methyl-8-azabicyclo[3.2.1]oct-2-ene benzoate 3-(5-methoxy-6-fluoroisoquinolin-3-yl)-8-methyl-8-azabicyclo[3.2.1]oct-2-ene 3-(6-cyclohexylisoquinolin-4-yl)-8-methyl-8-azabicyclo-[3.2.1]oct-2-ene hydrobromide 3-(6-hydroxyquinoxalin-2-yl)-8-methyl-8-azabicyclo-[3.2.1]oct-2-ene maleate The 3-(indol-3-yl)-8-azabicyclo[3.2.1]-oct-2-enes and 3-(indol-3-yl)-8-azabicyclo[3.2.1]octanes of the present invention are prepared by the method illustrated in Synthetic Scheme I. R is as previously defined.

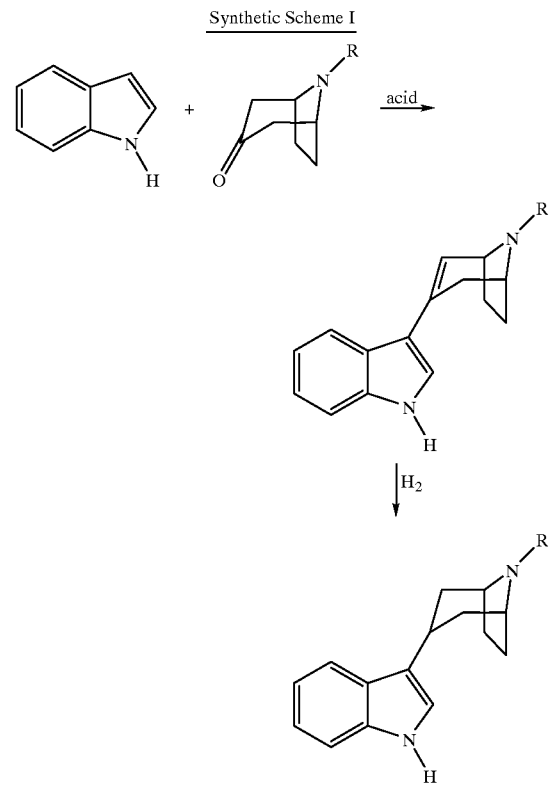

Synthetic Scheme I

The appropriate indole is condensed with a 3-tropanone (8-substituted-8-azabicyclo[3.2.1]oct-3-one) in the presence of a suitable acid to prepare the corresponding 3-(indol-3-yl)-8-azabicyclo[3.2.1]oct-2-ene. While most of the indoles required for the preparation of compounds of the present invention are commercially available, they may all be prepared by the Fischer indole synthesis as described in Robinson, *The Fischer Indole Synthesis*, Wiley, New York, 1983; Hamel, et al., *Journal of Organic Chemistry*, 59, 6372 (1994); and Russell, et al., *Organic Preparations and Procedures International*, 17, 391 (1985).

The reaction is performed by first dissolving the indole in a suitable solvent, typically acetic acid, and then adding a suitable acid, such as hydrochloric or phosphoric acid. The 3-tropanone is then added and the reaction heated at about 60–65° C. for from about 4 to about 24 hours. The resulting 3-(indol-3-yl)-8-azabicyclo-[3.2.1]oct-2-ene is isolated by pouring the reaction mixture into an ice water slurry, adjusting the pH of the aqueous mixture to about 8 by the addition of base, typically sodium hydroxide, and extracting with a water immiscible solvent, typically dichloromethane or ethyl acetate. The product recovered may be purified by crystallization or chromato-graphy as necessary or desired.

The 3-(indol-3-yl)-8-azabicyclo[3.2.1]oct-2-ene may be hydrogenated over a precious metal catalyst, such as palladium on carbon, to give the corresponding 3-(indol-3-yl)-8-azabicyclo[3.2.1]octane. For those compounds of the invention where the indole moiety is substituted with bromo, a hydrogenation catalyst such as sulfided platinum on carbon, platinum oxide, or a mixed catalyst system of sulfided platinum on carbon with platinum oxide is used to prevent hydrogenolysis of the bromo substituent during reduction of the octene double bond. The hydrogenation solvent may consist of a lower alkanol, such as methanol or ethanol, tetrahydrofuran, or a mixed solvent system of tetrahydrofuran and ethyl acetate. The hydrogenation may be performed at an initial hydrogen pressure of 20–80 p.s.i., preferably from 50–60 p.s.i., at 0–60° C., preferably at ambient temperature to 40° C., for 1 hour to 3 days. Additional charges of hydrogen may be required to drive the reaction to completion depending on the specific substrate. The compounds prepared in this manner are isolated by removal of the catalyst by filtration followed by concentration of the reaction solvent under reduced pressure. The product recovered may further purified by chromatography, or by recrystallization from a suitable solvent.

Alternatively, the 2-substituted-1H-indoles of the present invention may be prepared as described in Synthetic Scheme II. R* is $C_1$–$C_4$ alkyl or a nitrogen protecting group. Nitrogen protecting groups useful for these reactions are well known to the skilled artisan (Greene, *Protective Groups in organic Synthesis*, Second Edition, Wiley Interscience, New York (1991)). Preferred protecting groups are benzyl, and the $C_1$–$C_4$ alkoxycarbonyl groups, such as ethoxycarbonyl and t-butyloxycarbonyl.

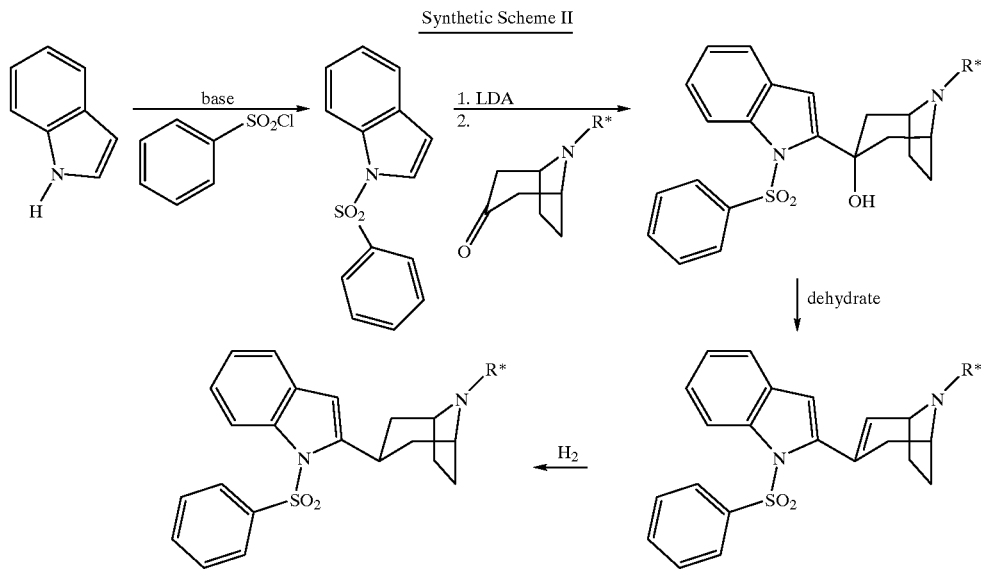

Synthetic Scheme II

An appropriate indole is N-deprotonated and the resulting anion reacted with phenylsulfonyl chloride to provide the corresponding 1-phenylsulfonylindole. This protected indole may be purified or treated directly with an appropriate base, typically a lithium amide such as lithium diisopropylamide, and then reacted with an appropriate tropanone to provide the corresponding 3-hydroxy-3-(1-phenylsulfonylindol-2-yl)-8-azabicyclo[3.2.1]oct-2-ane.

The phenylsulfonyl group may be removed by basic hydrolysis before or after acid catalyzed dehydration of the tertiary alcohol to the corresponding alkene of the present invention. The dehydration of the tertiary alcohol is accomplished by treatment with an acid in an appropriate solvent. Preferred solvents are toluene and dichlorometh-ane. The acid may be soluble in the reaction mixture or may be an acidic resin which is insoluble in the reaction mixture. Trifluoroacetic acid is a preferred soluble acid and AMBERLYST 15™ (Aldrich Chemical Company, P.O. Box 2060, Milwaukee, Wis. 53201, USA) is a preferred acidic resin. The dehydration reactions may be run at from about ambient temperature to the reflux temperature of the solvent. Once the dehydration is complete, the reaction mixture is concentrated under reduced pressure. In those cases where an acidic resin is used, it is more convenient to remove the resin by filtration prior to concentration of the reaction mixture under reduced pressure. The residue is then dissolved in a water immiscible solvent, such as dichloromethane, and the organic solution is washed with an aqueous base such as sodium bicarbonate solution. The remaining organic phase is dried and then concentrated under reduced pressure. The residue may be used directly in other reactions, converted to an appropriate salt, crystallized or purified by chromatography as desired. These may then be hydrogenated to the corresponding octane as described supra.

The compounds of the present invention where HET is benzothien-3-yl are prepared by the method illustrated in Synthetic Scheme III where R* is as previously defined.

Synthetic Scheme III

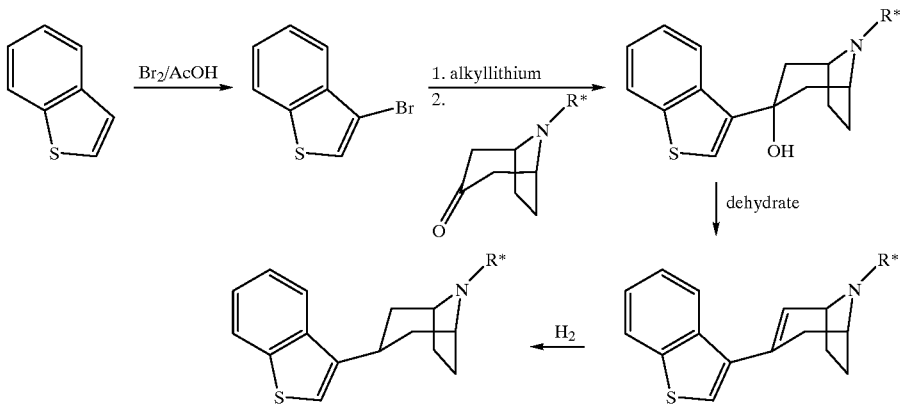

A suitable benzothiophene is selectively brominated with bromine in acetic acid. The reaction is typically performed at about 50° C. for about 4 hours. The volatiles are then removed under reduced pressure and the residue is subjected to an extractive workup under basic conditions. The resulting 3-bromobenzothiophene in diethyl ether is then treated with an alkyllithium, typically n-butyllithium, in the same solvent, at −78° C. After stirring at this temperature for about 1 hour, the reaction mixture is treated with an equivalent of an appropriate tropanone. Once the addition of the 3-tropanone is complete, the reaction mixture is stirred at −78° C. for an additional 3 hours. It is critical to maintain the reaction mixture at this temperature to avoid equilibration of the anion to the 2-position of the benzothiophene ring. The reaction mixture is then allowed to warm to −20° C. over about 50 minutes. The reaction mixture is then quenched with saturated aqueous sodium bicarbonate and is then diluted with 1:1 hexane:di-ethyl ether. The resulting mixture is washed with brine, the organic phase dried and then concentrated under reduced pressure. The resulting tertiary alcohol may be used directly for the subsequent dehydration step as described supra, or first purified by chromatography or crystalliza-tion as appropriate. The corresponding octanes may be prepared by reduction by the conditions described supra.

The 2-benzothiophenes of the present invention are prepared by the method illustrated in Synthetic Scheme IV where R* is as previously defined.

Synthetic Scheme IV

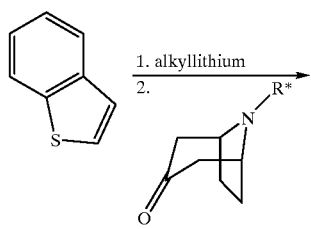

-continued

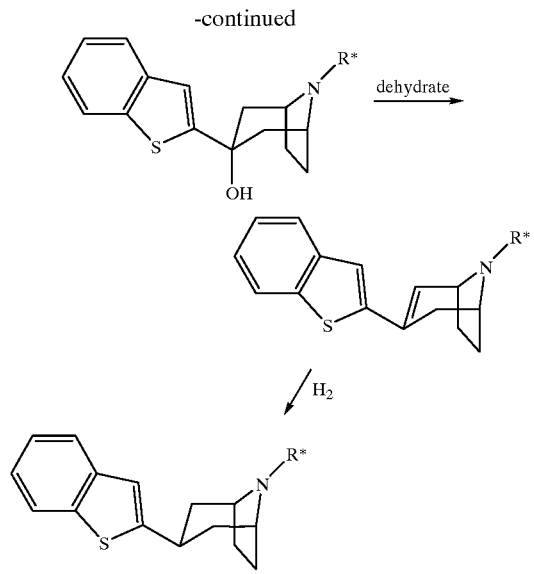

An appropriate benzothiophene is treated with an alkyllithium, typically n-butyllithium, in a suitable solvent, preferably tetrahydrofuran or diethyl ether, at −78° C. After stirring at this temperature for about 1 hour, the reaction mixture is treated with an equivalent of an appropriate 3-tropanone. Once the addition of the tropanone is complete, the reaction mixture is allowed to warm to about 0° C. The reaction mixture is then quenched with saturated aqueous sodium bicarbonate and is then diluted with 1:1 hexane:di-ethyl ether. The resulting mixture is washed with brine, the organic phase dried and then concentrated under reduced pressure. The resulting tertiary alcohol may be used directly for the subsequent dehydration step or first purified by chromatography or crystallization as appropriate. The dehydration and subsequent reduction steps are performed as described supra to prepare the desired compounds of the invention.

The benzothiophenes required for the preparation of the compounds of this invention are either commercially available or may be prepared by methods well known to the skilled artisan. For example, Method (a) of Synthetic Scheme VI is that of Beck et al. (*Journal of Organic Chemistry*, 37(21), 3224 (1972)); and Method (b) of is that of Bridges et al., *Tetrahedron Letters*, 33(49), 7499 (1992).

An alternate route to the same methyl benzothiophene-2-carboxylate is illustrated by method (b) of Synthetic Scheme V. This method exploits the facility with which an aromatic nitro group can undergo nucleophilic displacement. A suitable o-nitrobenzaldehyde is treated with an equimolar

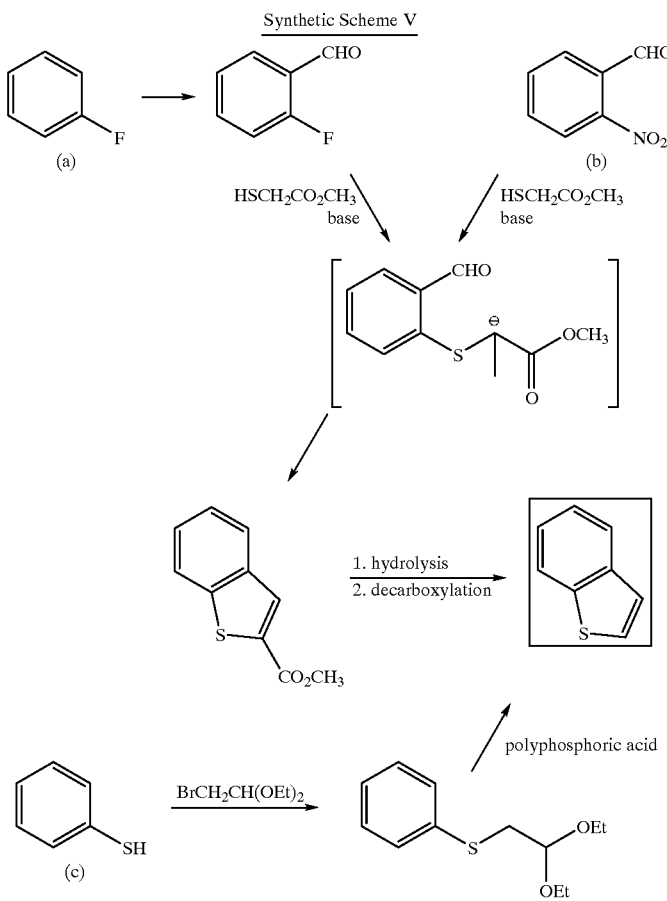

The three methods described in Synthetic Scheme V provide the requisite benzothiophenes from three different structural classes of starting materials. The selection of a particular method is dependent upon the availability of starting materials and the stability of the substituents to the particular reaction conditions.

Method (a) of Synthetic Scheme V takes advantage of the relative acidity of aromatic protons adjacent to a carbon bearing a fluorine atom. Treatment of an appropriate fluorobenzene with a suitable base followed by addition of dimethylformamide provides, after an aqueous acid workup, the corresponding fluorobenzaldehyde. Suitable bases for this transformation include alkyllithiums such as n-butyllithium or sec-butyllithium, and lithium amides such as lithium 2,2,6,6-tetramethylpiperidide or lithium diisoprop-ylamide. The resulting fluorobenzaldehyde is treated with the anion of methyl thioglycollate. This anion may first be formed by treatment of a solution of methyl thioglycollate in dimethylsulfoxide with a metal hydride, preferably sodium hydride, and then adding the fluorobenzaldehyde. The exothermic reaction provides the corresponding methyl benzothiophene-2-carboxylate. Alternatively, the fluorobenzaldehyde, methyl thioglycollate and a suitable tertiary amine, preferably triethylamine, are heated together in dimethylsulfoxide to prepare the corresponding methyl benzothiophene-2-carboxylate.

amount of methyl thioglycollate and potassium carbonate in dimethylformamide.

The methyl benzothiophene-2-carboxylates prepared by either of these two methods is converted to the required benzothiophene by standard ester hydrolysis/decarboxylation steps. A solution of the appropriate ester in a lower alkanol, typically methanol or ethanol, is treated with a small excess of sodium or potassium hydroxide. Once the hydrolysis is complete, volatiles are removed under reduced pressure. The residue is taken up in quinoline and to this mixture is added elemental copper. The reaction mixture is then heated to about 200° C. until the decarboxylation is complete. The desired product is isolated by normal extractive techniques and may be purified by chromatography or crystallization as appropriate prior to subsequent use.

Method (c) provides the requisite benzothiophenes from appropriately substituted thiophenols, including aminothiophenols. A solution of the thiophenol in an appropriate solvent, such as acetone, tetrahydrofuran or diethyl ether, is treated with potassium carbonate followed by bromoacetaldehyde diethyl acetal. The resulting mixture is stirred at about ambient temperature for from 1 hour to about 48 hours until the reaction is complete. The reaction mixture is then filtered and the filtrate concentrated under reduced pressure. The residue is subjected to an extractive workup and the product may be used directly in the subse-quent step or purified by chromatography or crystallization if desired. This material is then dissolved in an appropri-ate solvent, typically a halobenzene such as chlorobenzene, and is treated with polyphosphoric acid. The reaction is heated to reflux until the cyclization is complete. The desired benzothiophene may be isolated by normal extractive workups. In those cases where substituents on the benzene ring are such that isomeric benzothiophenes may result from the cyclization, the isomers may be separated by chromatographic or crystallization techniques at this or any subsequent convenient point in the synthetic pathway to compounds useful for the method of the present invention.

The compounds of the invention may also be prepared from the corresponding HET-halide as illustrated in Synthetic Scheme VI, where halide is chloro, bromo or iodo and R* and HET are as previously defined.

Synthetic Scheme VI

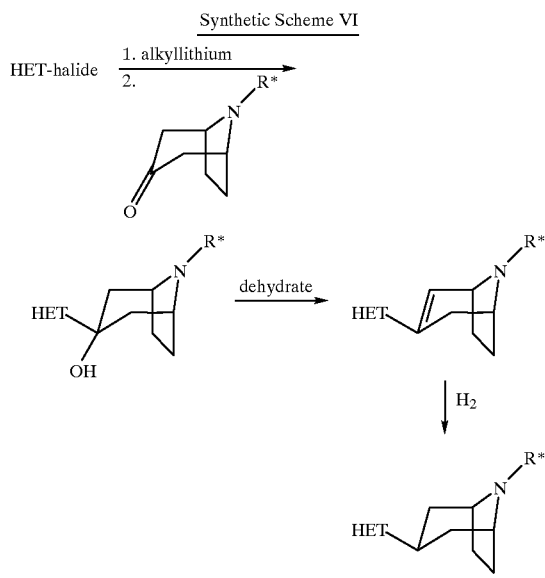

An appropriate HET-halide is reacted with an alkyllith-ium, typically n-butyllithium or sec-butyllithium, at about −78° C. for from 1 to about 4 hours in a suitable solvent, such as diethyl ether or tetrahydrofuran. To the HET-Li formed in this manner is added an appropriate tropanone and the reaction is stirred from about 4 to about 24 hours at room temperature. The resultant alcohol is isolated by extractive workup may be used as isolated for subsequent reactions or purified by chromatography if necessary. The alcohol is dehydrated and subsequently hydrogenated as previously described to provide additional compounds of the invention.

Alternatively, compounds of the present invention may be prepared as illustrated in Synthetic Scheme VII where halide and HET are as previously defined.

Synthetic Scheme VII

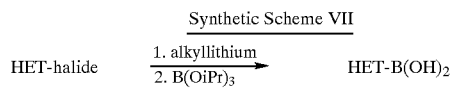

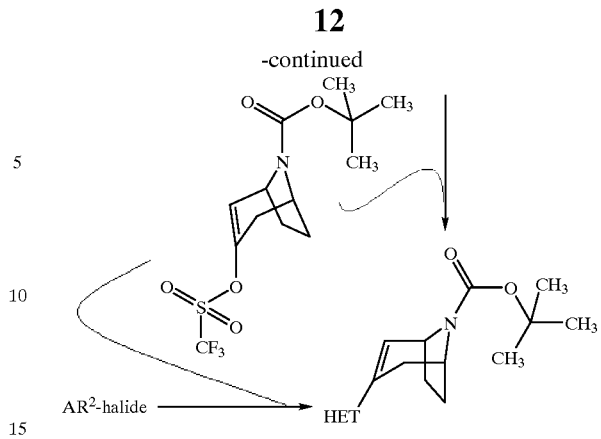

The HET-halide is reacted with an alkyllithium, typically n-butyllithium or sec-butyllithium, at about −78° C. for from 1 to about 4 hours in a suitable solvent, such as diethyl ether or tetrahydrofuran. To the HET-Li formed in this manner is added triisopropylborate and the reaction is stirred from about 4 to about 24 hours at room temperature. The resultant boronic acid and 8-tert-butoxycarbonyl-3-trifluoromethanesulfonyloxybicyclo-[3,2,1]oct-2-ene are reacted together with [1, 1-bis(diphenylphosphino)-1-ferrocene]palladium II chloride in tetrahydrofuran containing lithium chloride, aqueous sodium carbonate and methanol. The reaction is performed at about reflux for from about 1 to about 12 hours. The desired alkene is isolated by standard extractive work up and may be used as isolated or purified by chromatography if necessary or desired. The resultant alkene may then be hydrogenated as previously described to prepare additional compounds of the invention.

A further alternative for synthesis of the compounds of the present invention, particularly where HET is quinoxalin-2-yl, the HET-halide is coupled directly with 8-tert-butoxycarbonyl-3-trifluoromethanesulfonyloxy-bicyclo[3,2,1]oct-2-ene in the presence of hexamethyl-ditin and [tetrakis(triphenylphosphine)]palladium in 1,4-dioxane containing lithium chloride. The reaction is performed at reflux for about 18 hours. The desired alkene is isolated by the procedures previously described.

The requisite 8-tert-butoxycarbonyl-3-trifluoromethanesulfonyloxybicyclo-[3,2,1]oct-2-ene is prepared by reacting 8-tert-butoxycarbonyltropan-3-one with an equivalent of freshly prepared lithium diisopropylamide. The resulting enolate is reacted with N-phenyltrifluoromethanesulfonimide. The product is isolated by concentrating the reaction mixture under reduced pressure and subjecting the resultant residue to chromatography on neutral alumina.

The previous schemes illustrate chemistry performed on unsubstituted heterocycles. The skilled artisan will appreciate that the chemistry as illustrated also applies to those heterocycles bearing allowed substituents. The skilled artisan will also appreciate that not all of the possible HET substituents will survive the anion chemistry described supra. The preparation of compounds containing functionality sensitive to anion chemistry may be accomplished by the use of an appropriate amino-substituted substrate. Once the anion chemistry is completed, the amino group may be diazotized and displaced under standard methods to provide the appropriate halo or cyano substituted compound. The nitrile may be hydrated to the carboxamide if desired. Those compounds of the present invention where HET is substituted by hydroxy are easily prepared by trimethylsilyl iodide cleavage of the corresponding alkoxy compound, or catalytic O-debenzylation of the corresponding benzyloxy compound. Furthermore, compounds of this invention where R is hydrogen may be prepared from the corresponding N-benzylated compound. Either of these hydrogenolyses may be performed by dissolution of an appropriate substrate in a lower alkanol, such as methanol or ethanol, tetrahydrofuran or a mixed solvent system of tetrahydrofuran and ethyl acetate. The hydrogenation may be performed at an initial hydrogen pressure of 20–80 p.s.i., preferably from 50–60 p.s.i., at 0–60° C., preferably at ambient temperature to 40° C., for 1 hour to 3 days. Additional charges of hydrogen may be required to drive the reaction to completion depending on the specific substrate. Compounds prepared in this manner are isolated by removal of the catalyst by filtration followed by concentration of the reaction solvent under reduced pressure. The product recovered may be purified by chromatography or recrystallization from a suitable solvent if necessary. Furthermore, where R* is a nitrogen-protecting group, the protecting group may be removed at any convenient point in the synthesis by chemistry well known in the art. Where R* is tert-butyloxycarbonyl, for example, it may be removed by treatment with trifluoroacetic acid alone or in the presence of a mutual solvent such as dichloromethane.

The following preparations and examples further illustrate the synthesis of the compounds of this invention and are not intended to limit the scope of the invention in any way. The compounds described below were identified by various standard analytical techniques as stated in the individual preparations and examples.

PREPARATION I
3-bromo-5-chlorobenzothiophene

To a solution of 0.30 gm (1.77 mMol) 5-chlorobenzothiophene 1.0 mL acetic acid was added a solution of 0.31 gm (1.95 mMol) bromine in 1.0 mL acetic acid under a nitrogen atmosphere. The reaction was heated to 50° C. for 4 hours at which time the volatiles were removed under reduced pressure. The residue was partitioned between dichloromethane and aqueous sodium bicarbonate. The phases were separated and the organics were washed with saturated aqueous sodium chloride, dried over sodium sulfate and concentrated under reduced pressure to give 0.335 gm (76%) of the title compound as a tan solid.
m.p.=85–86° C.
MS(FD): m/e=249 (M+2)
EA: Calculated for: $C_8H_4BrClS$: Theory: C, 38.82; H, 1.63. Found: C, 39.12; H, 1.72.

PREPARATION II
1:1 mixture of 4-chloro-:6-chlorobenzothiophene 2-(3-chlorophenylthio)acetaldehyde diethyl acetal To a stirring mixture of 20.0 gm (0.138 mol) 3-chlorothiophenol and 21.0 gm (0.15 mol) potassium carbonate in 220 mL acetone were added dropwise 1.1 equivalents of bromoacetaldehyde diethyl acetal. After stirring for 17 hours at ambient temperature, the reaction mixture was filtered and the filtrate concentrated under reduced pressure. The resulting residue was partitioned between diethyl ether and water. The organic phase was separated, washed with saturated sodium chloride, dried over sodium sulfate and concentrated under reduced pressure to give 35.1 gm (97%) of the desired compound as a rust colored oil.
MS(FD): m/e=260 (M+)
EA: Calculated for: $C_{12}H_{17}O_2ClS$: Theory: C, 55.27; H, 6.57. Found: C, 55.37; H, 6.35.
Cyclization To a mixture of 12.8 gm polyphosphoric acid in 100 mL refluxing chlorobenzene were added dropwise a solution of 6.0 gm (0.023 mol) 2-(3-chlorophenylthio) acetaldehyde diethyl acetal in 20 mL chlorobenzene. The resulting slurry was stirred at reflux for 1 hour and was then cooled to ambient temperature. The organics were decanted, washed with saturated aqueous sodium chloride, dried over sodium sulfate and concentrated under reduced pressure to give 2.75 gm (71%) of the title mixture as a rust-colored oil. This material was suitable for subsequent steps without further purification.

PREPARATION III
4-cyclopropylmethoxy-1H-indole

A solution of 5.00 gm (37.6 mMol) 4-hydroxyindole in dimethylformamide was added dropwise over 30 minutes to a solution of 1.65 gm (41.3 mMol) sodium hydride (60% suspension in mineral oil) in 25 mL dimethylformamide at 0° C. The resulting black solution was stirred at room temperature for 2 hours and then a solution of 3.6 mL (37.6 mMol) cyclopropylmethyl bromide in 10 mL dimethylformamide was added dropwise. The resulting mixture was stirred for 1.5 hours at room temperature. The reaction mixture was then quenched by the addition of 100 mL water and the resulting mixture extracted well with ethyl acetate. The organic phases were combined, washed sequentially with water and saturated aqueous sodium chloride, dried over sodium sulfate and concentrated under reduced pressure. The residue was subjected to silica gel chromatography, eluting with 10% ethyl acetate in hexane. Fractions shown to contain product were combined and concentrated under reduced pressure to provide 4.48 gm (64%) of the title compound as an amber oil.

PREPARATION IV
3-bromo-6-chlorobenzothiophene

A solution of 1.41 gm (8.9 mMol) bromine in 5 mL acetic acid was added dropwise to a solution of 3.0 gm (17.8 mMol) of a 1:1 mixture of 4- and 6-chlorobenzothiophene (Preparation IV) in 10 mL acetic acid. The reaction mixture was stirred at 50° C. for about 4 hours. The reaction mixture was then concentrated under reduced pressure and the residue dissolved in dichloromethane. The organic solution was then washed sequentially with saturated aqueous sodium bicarbonate and saturated aqueous sodium chloride. The remaining organics were dried over sodium sulfate and concentrated under reduced pressure to provide a red oil which crystallized upon standing. This residue was recrystallized from pentane to provide 0.78 gm (35%) of the title compound as a colorless solid.
MS(FD): m/e=246 (M+)
EA: Calculated for: $C_8H_4ClBrS$: Theory: C, 38.82; H, 1.63. Found: C, 39.05; H, 1.72.

PREPARATION V
1-phenylsulfonyl-1H-indole

A solution of 5.0 gm (42.7 mMol) indole in 60 mL tetrahydrofuran was cooled to −78° C. and to it was added a solution of 28 mL (44.8 mMol) n-butyllithium (1.6 M in hexane) via syringe. The cooling bath was removed and the reaction mixture stirred for 1 hour. At this point the reaction mixture was again cooled to −78° C. and to it was added 6.5 mL phenylsulfonyl chloride. The reaction mixture was then to warm to room temperature over 18 hours. The reaction mixture was then partitioned between saturated aqueous sodium bicarbonate and diethyl ether. The phases were separated and the organic phase washed with saturated aqueous sodium chloride, dried over sodium sulfate and concentrated under reduced pressure to provide 7.85 gm (71%) of the desired compound as a white solid.

PREPARATION VI
3-trifluoromethanesulfonyloxy-8-methyl-8-azabicyclo[3.2.1]oct-2-ene A solution of diisopropylamine in tetrahydrofuran is cooled to −78° C. To this solution is added dropwise n-butyllithium (1.6 M in hexanes) and the reaction mixture is stirred for 1.5 hours at −78° C. and is then allowed to warm to room temperature. The resulting solution is cooled again to −78° C. and then a solution of 8-methyl-8-azabicyclo[3.2.1]oct-3-one in tetrahydrofuran is added dropwise. After about 30 minutes, a solution of N-phenyltrifluoromethanesulfonimide in tetrahydrofuran is added dropwise. The reaction mixture is allowed to warm gradually to room temperature and is then concentrated under reduced pressure. The residue is dissolved in dichloromethane and placed on a pad of neutral alumina. The alumina column is eluted with 9:1 hexane:ethyl acetate. Fractions containing product are combined and concentrated under reduced pressure to provide title compound.

EXAMPLE 1
3-(6-fluoroindol-3-yl)-8-methyl-8-azabicyclo[3.2.1]oct-2-ene

A solution of 2.0 gm (14.8 mMol) 6-fluoroindole in 50 mL acetic acid was heated to 55° C. and vigorously deoxygenated with nitrogen. To this reaction mixture were then added 4.12 gm (29.6 mMol) tropinone and 12.3 mL 2N phosphoric acid. The resulting mixture was heated at 60–65° C. for 24 hours. The reaction mixture was cooled to room temperature and then poured into ice containing about 300 mL acetic acid. The pH of this mixture was then adjusted to about 8 by the addition of 50% aqueous NaOH. The resulting mixture was extracted well with dichloromethane. The combined organic extracts were washed with saturated aqueous sodium chloride, dried over magnesium sulfate, and concentrated under reduced pressure. The residue was subjected to silica gel chromatography, eluting with a gradient of dichlorometh-ane containing 30% dichloromethane saturated with ammonia and from 1–15% methanol. Fractions containing product were combined and concentrated under reduced pressure. The solid residue was crystallized from ethanol to provide 0.358 gm (9.44%) of the title compound as colorless crystals.

m.p.=226–227° C.

MS(FD): m/e=256 (M$^+$)

EA: Calculated for: $C_{16}H_{17}N_2F$: Theory: C, 74.97; H, 6.69; N, 10.93. Found: C, 75.05; H, 6.71; N, 10.95.

EXAMPLE 2
3-(6-fluoroindol-3-yl)-8-methyl-8-azabicyclo[3.2.1]octane

A mixture of 0.233 gm (0.91 mMol) 3-(6-fluoroindol-3-yl)-8-methyl-8-azabicyclo[3.2.1]oct-2-ene and 0.235 gm 10% palladium on carbon in 12 mL methanol was placed under an atmosphere of hydrogen at room temperature. After 8 hours the reaction mixture was filtered and then concentrated under reduced pressure. The residue was again hydrogenated with 0.23 gm 10% palladium on carbon in 7 mL ethanol. After several hours the reaction mixture was filtered and the filtrate concentrated under reduced pressure. The residue was subjected to basic alumina chromatography, eluting with dichloromethane containing 30% dichloromethane saturated with ammonia and 0.5–2% methanol. Fractions containing product were combined and concentrated under reduced pressure to provide 0.068 gm (29%) of the title compound as a colorless solid.

m.p.=168–169° C.

MS(FD): m/e=258 (M$^+$)

EA: Calculated for: $C_{16}H_{19}N_2F$: Theory: C, 74.39; H, 7.41; N, 10.84. Found: C, 74.61; H, 7.54; N, 10.83.

EXAMPLE 3
3-(naphth-2-yl)-8-methyl-8-azabicyclo[3.2.1]oct-2-ene trifluoroacetate A solution of 5.0 gm (24.1 mMol) 2-bromonaphthalene in 80 mL tetrahydrofuran was cooled to −78° C. To this solution was then added 15.8 mL (25.3 mMol) n-butyllithium (1.6M in tetrahydrofuran) followed by a solution of 4.03 gm (29 mMol) 3-tropinone in 35 mL tetrahydrofuran. The reaction mixture was stirred at −78° C. for 2 hours and was then allowed to warm gradually to room temperature. The reaction mixture quenched by the addition of saturated aqueous ammonium chloride. The resulting mixture was extracted well with ethyl acetate. The organic phases were combined, dried over magnesium sulfate and concentrated under reduced pressure. The residue was subjected to silica gel chromatography, eluting with dichloromethane containing from 2–10% methanol and 30% dichloromethane saturated with ammonia. Fractions containing product were combined and concentrated under reduced pressure to provide 3.2 gm (50%) of 3-hydroxy-3-(naphth-2-yl)-8-methyl-8-azabicyclo[3.2.1]octane.

MS(FD): m/e=267 (M$^+$)

EA: Calculated for: $C_{18}H_{21}NO$: Theory: C, 80.86; H, 7.92; N, 5.24. Found: C, 80.65; H, 8.04; N, 5.16.

A solution of 1.8 gm (6.74 mMol) 3-hydroxy-3-(naphth-2-yl)-8-methyl-8-azabicyclo[3.2.1]octane and 15 mL trifluoroacetic acid in 70 mL dichloromethane was stirred at room temperature for 2 hours. The reaction mixture was then concentrated under reduced pressure. The residue was dissolved in ethyl acetate and this solution was then washed sequentially, with saturated aqueous sodium bicarbonate, water, and saturated aqueous sodium chloride. The organic phase was dried over magnesium sulfate and then concentrated under reduced pressure. The residue was subjected to silica gel chromatography, eluting with a gradient of dichloromethane containing 30% dichloromethane saturated with ammonia and from 3–7% methanol. Fractions containing product were combined and concentrated under reduced pressure. The residue was dissolved in ethyl acetate and a solid triturated by the addition of hexane. The triturated solid was filtered and dried to provide 1.2 gm (49%) of the title compound as a light tan solid.

m.p.=146–148° C.

MS(FD): m/e=249(M$^+$)

EA: Calculated for: $C_{18}H_{19}N$—$CHF_3O_2$: Theory: C, 66.11; H, 5.55; N, 3.86; F, 15.68. Found: C, 65.87; H, 5.30; N, 4.07; F, 15.56.

EXAMPLE 4
3-(naphth-2-yl)-8-methyl-8-azabicyclo[3.2.1]octane

A solution of 1.3 gm (5.22 mMol) 3-(naphth-2-yl)-8-methyl-8-azabicyclo[3.2.1]oct-2-ene in 25 mL ethanol containing 1.3 gm 10% palladium on carbon was stirred at room temperature under a hydrogen atmosphere maintained by a balloon for 8 hours. The reaction mixture was filtered and the filtrate concentrated under reduced pressure. The residue was subjected to silica gel chromatography, eluting with a gradient of dichloromethane containing 2–10% methanol and 30% of dichloromethane saturated with ammonia. Fractions containing product were combined and concentrated under reduced pressure to provide 0.020 gm (1.7%) of the title compound as a white solid.

m.p.=77–79° C.

MS(FD): m/e=251(M$^+$)

EA: Calculated for: $C_{18}H_{21}N$: Theory: C, 86.01; H. 8.42; N, 5.57. Found: C, 86.03; H, 8.22; N, 5.68.

EXAMPLE 5
3-(naphth-2-yl)-8-ethoxycarbonyl-8-azabicyclo[3.2.1]oct-2-ene

Beginning with 18.0 gm (91 mMol) 8-ethoxycarbonyl-8-azabicyclo[3.2.1]oct-3-one and 18.9 gm (91 mMol) 2-bromonaphthalene, 9.02 gm (32%) of the title compound was recovered as a yellow oil by the procedure described in detail in Example 3.

EXAMPLE 6

3-(naphth-2-yl)-8-azabicyclo[3.2.1]oct-2-ene

A mixture of 5.0 gm (16.3 mMol) 3-(naphth-2-yl)-8-ethoxycarbonyl-8-azabicyclo[3.2.1]oct-2-ene, 4.07 gm (81.3 mMol) hydrazine hydrate, and 5.49 gm (97.8 mMol) potassium hydroxide in 120 mL ethylene glycol was heated at reflux for 2 hours. The reaction mixture was allowed to cool gradually to room temperature. After 16 hours the reaction mixture was poured into water and extracted well with diethyl ether. The organic phase was dried over sodium sulfate and concentrated under reduced pressure. The residue was dissolved in 1N hydrochloric acid and the solution washed with diethyl ether. The aqueous phase was basified and the mixture extracted well with ethyl acetate. The organic phase was dried over sodium sulfate and concentrated under reduced pressure to provide the title compound as a yellow oil.

EXAMPLE 7

3-(naphth-2-yl)-8-azabicyclo[3.2.1]octane oxalate

A mixture of 4.0 gm (13.0 mMol) 3-(naphth-2-yl)-8-ethoxycarbonyl-8-azabicyclo[3.2.1]oct-2-ene, 0.5 gm 10% palladium on carbon and 8.22 gm (130 mMol) ammonium formate in 100 mL ethanol was stirred at room temperature for 16 hours and then at reflux for 1.5 hours. The reaction mixture was filtered and the filtrate concentrated under reduced pressure. The residue was subjected to silica gel chromatography. Fractions containing product were combined and concentrated under reduced pressure to provide 2.83 gm (70.4%) of 3-(naphth-2-yl)-8-ethoxycarbonyl-8-azabicyclo-[3.2.1]octane.

A mixture of 2.64 gm (8.53 mMol) 3-(naphth-2-yl)-8-ethoxycarbonyl-8-azabicyclo[3.2.1]octane, 2.14 gm (42.7 mMol) hydrazine hydrate, and 2.87 gm (51.2 mMol) potassium hydroxide in 70 mL ethylene glycol was heated at reflux for 2 hours. The reaction mixture was allowed to cool gradually to room temperature, poured into water and extracted well with diethyl ether. The organic phase was dried over sodium sulfate and concentrated under reduced pressure. The residue was treated with oxalic acid to provide the title compound.

m.p.=218–220° C.

EXAMPLE 8

3-(indol-2-yl)-8-methyl-8-azabicyclo[3.2.1]oct-2-ene

A solution of 1 equivalent of lithium diisopropylamide (15.5 mMol in tetrahydrofuran) is added via cannula to a solution of 1 equivalent of 1-phenylsulfonyl-1H-indole in tetrahydrofuran at −78° C. The reaction mixture is stirred at this temperature for 1.5 hours, warmed to room temperature for 1 hour and then cooled again to −78° C. To this solution is then added a solution of 1.02 equivalents of 3-tropanone in tetrahydrofuran and the resulting mixture is allowed to warm to room temperature over 18 hours. The reaction mixture is then partitioned between saturated aqueous sodium bicarbonate and diethyl ether. The phases are separated and the organic phase washed with saturated aqueous sodium chloride, dried over sodium sulfate and concentrated under reduced pressure. The residue is subjected to silica gel chromatography. Fractions shown to contain product are combined and concentrated under reduced pressure to provide 3-hydroxy-3-(1-phenylsulfonylindol-2-yl)-8-methyl-8-azabicyclo-[3.2.1]octane.

A solution of 3-hydroxy-3-(1-phenylsulfonylindol-2-yl)-8-methyl-8-azabicyclo[3.2.1]octane and trifluoroacetic acid in dichloromethane is stirred at room temperature until the dehydration is complete. The reaction mixture is concentrated under reduced pressure and the residue partitioned between dichloromethane and saturated aqueous sodium bicarbonate. The organic phase is separated, washed well with water, washed with saturated aqueous sodium chloride, dried over magnesium sulfate and concentrated under reduced pressure to provide the desired compound.

Deprotection

A solution of 3-(1-phenylsulfonylindol-2-yl)-8-methyl-8-azabicyclo[3.2.1]oct-2-ene in ethanol containing 2N sodium hydroxide is heated at reflux until the disappearance of starting material as measured by thin layer chromatography. The reaction mixture is cooled to room temperature and concentrated under reduced pressure. The residue is partitioned between ethyl acetate and 2N sodium hydroxide. The phases are separated and the organic phase is washed with saturated aqueous sodium chloride, dried over sodium sulfate and concentrated under reduced pressure. The residue is subjected to silica gel chromatography. Fractions shown to contain product are combined and concentrated under reduced pressure to provide the title compound.

EXAMPLE 9

3-(5-chlorobenzothien-2-yl)-8-methyl-8-azabicyclo[3.2.1]oct-2-ene

A solution of 5-chlorobenzothiophene in tetrahydrofuran is cooled to −78° C. To the cooled solution is then added n-butyllithium (1.2 M in tetrahydrofuran) and the reaction mixture stirred for 1 hour after the addition is complete. To this solution is added 8-methyl-8-azabicyclo[3.2.1]oct-3-one and the reaction mixture is allowed to warm to 0° C. The reaction mixture is quenched with saturated aqueous sodium bicarbonate and partitioned by the addition of hexane/diethyl ether. The organic phase is washed with saturated aqueous sodium chloride, dried over sodium sulfate and concentrated under reduced pressure. This residue is subjected to silica gel chromatography. Fractions containing product are combined and concentrated under reduced pressure to provide 3-hydroxy-3-(5-chlorobenzothien-2-yl)-8-methyl-8-azabicyclo[3.2.1]oct-2-ene. This alcohol is reacted with trifluoroacetic acid as described in Example 8 to prepare the title compound.

EXAMPLE 10

3-(6-chlorobenzothien-3-yl)-8-methyl-8-azabicyclo[3.2.1]oct-2-ene

A solution of n-butyllithium in diethyl ether is cooled to −78° C. under a nitrogen atmosphere. To this cooled solution is added a solution of 3-bromo-6-chlorobenzothio-phene in diethyl ether. The reaction mixture is stirred at −78° C. for 1 hour and then to it is added dropwise a solution of 8-methyl-8-azabicylo[3.2.1]oct-3-one in diethyl ether and the reaction is stirred an additional 2 hours at −78° C., then is warmed to −20° C. over 55 minutes. The reaction mixture is then quenched with saturated aqueous sodium bicarbonate, diluted with additional diethyl ether and the phases separated. The organic phase is washed with saturated aqueous sodium chloride, dried over sodium sulfate and concentrated under reduced pressure. The residue is subjected to flash silica chromatography. Fractions shown to contain product are combined and concentrated under reduced pressure to provide 3-hydroxy-3-(6-chlorobenzothien-3-yl)-8-methyl-8-azabicyclo[3.2.1]oct-2-ene. This alcohol is reacted with trifluoroacetic acid as described in Example 8 to prepare the title compound.

EXAMPLE 11
3-(isoquinolin-4-yl)-8-methyl-8-azabicyclo[3.2.1]octane

A solution of 4-bromoisoquinoline in tetrahydrofuran is cooled to −78° C. To this solution is added dropwise n-butyllithium (1.6 M in hexane), and the resultant solution is stirred for 30 minutes. To this solution is then added dropwise triisopropylborate and the reaction mixture is then stirred for 18 hours at room temperature. The reaction mixture is then partitioned between ethyl acetate and saturated aqueous sodium chloride. The phases are separated and the aqueous phase extracted well with ethyl acetate. The combined organic phases are washed with saturated aqueous sodium chloride, dried over sodium sulfate and concentrated under reduced pressure. The residue is sonicated in a mixture of hexane:ethyl acetate. The resulting suspension is filtered to provide isoquinolin-4-ylboronic acid.

A mixture of isoquinolin-4-ylboronic acid, 3-trifluoromethanesulfonyloxy-8-methyl-8-azabicyclo[3.2.1]-oct-2-ene, lithium chloride, [1,1'-bis(diphenylphosphino)-1-ferrocene]-palladium II chloride, and 2M aqueous sodium carbonate in tetrahydrofuran containing a few drops of methanol is stirred at reflux for about 4 hours. The reaction is cooled to room temperature and then partitioned between ethyl acetate and 2N sodium hydroxide. The phases are separated and the aqueous phase extracted well with ethyl acetate. The organic phases are combined, washed with saturated aqueous sodium chloride, dried over sodium sulfate and concentrated under reduced pressure. The residue is subjected to flash silica gel chromatography. Fractions containing product are combined and concentrated under reduced pressure to provide 3-(isoquinolin-4-yl)-8-methyl-8-azabicyclo[3.2.1]oct-2-ene.

A mixture 3-(isoquinolin-4-yl)-8-methyl-8-azabicyclo[3.2.1]oct-2-ene and 5-palladium on carbon in methanol is stirred at room temperature for 3 days under a hydrogen atmosphere. The reaction mixture is then filtered and the filtrate concentrated under reduced pressure. The residue is subjected to flash silica gel chromatography. Fractions containing product are combined and concentrated under reduced pressure to provide the title compound.

EXAMPLE 12
3-(quinoxalin-2-yl)-8-methyl-8-azabicyclo[3.2.1]oct-2-ene

A mixture of 2-chloroquinoxaline, 3-trifluoromethanesulfonyloxy-8-methyl-8-azabicyclo[3.2.1]-oct-2-ene, hexamethylditin, lithium chloride, and [tetrakis(triphenylphosphine)]palladium in dioxane is stirred at reflux for 18 hours. The reaction mixture is cooled to room temperature and then poured into a mixture of saturated aqueous potassium fluoride and ethyl acetate. After stirring for two hours, the phases are separated. The organic phase is washed with saturated aqueous sodium chloride, dried over magnesium sulfate and concentrated under reduced pressure. The residue is subjected to flash silica gel chromatography. Fractions containing product are combined and concentrated under reduced pressure to provide the title compound.

The efficacy of the compounds of Formula I to inhibit the reuptake of serotonin has been determined by a paroxetine binding essay, the usefulness of which is set out by Wong, et al., *Neuropsychopharmacology*, 8, 23–33 (1993). Synaptosomal preparations from rat cerebral cortex were made from the brains of 100–150 g Sprague-Dawley rats which were killed by decapitation. The cerebral cortex was homogenized in 9 volumes of a medium containing 0.32 M sucrose and 20 $\mu$M glucose. The preparations were resuspended after centrifugation by homogenizing in 50 volumes of cold reaction medium (50 $\mu$M sodium chloride, 50 $\mu$M potassium chloride, pH 7.4) and centrifuging at 50,000 g for 10 minutes. The process was repeated two times with a 10-minute incubation at 37° C. between the second and third washes. The resulting pellet was stored at −70° C. until use. Binding of $^3$H-paroxetine to 5-HT uptake sites was carried out in 2 ml reaction medium containing the appropriate drug concentration, 0.1 nM $^3$H-paroxetine, and the cerebral cortical membrane (50 $\mu$g protein/tube). Samples were incubated at 37° C. for 30 minutes; those containing 1 $\mu$M fluoxetine were used to determine nonspecific binding of $^3$H-paroxetine. After incubation, the tubes were filtered through Whatman GF/B filters, which were soaked in 0.05% polyethylenimine for 1 hour before use, using a cell harvester by adding about 4 ml cold Tris buffer (pH 7.4), aspirating, and rinsing the tubes three additional times. Filters were then placed in scintillation vials containing 10 ml scintillation fluid, and the radioactivity was measured by liquid scintillation spectrophotometry.

Results of testing representative compounds of Formula I by the above method showed potent reuptake activity, in some cases activity in the low nanomolar range.

The pharmacological activities which have been described immediately above provide the mechanistic basis for the pharmaceutical utility of the compounds described in this document. A number of pharmaceutical utilities will be described below.

Throughout this document, the person or animal to be treated will be described as the "subject", and it will be understood that the most preferred subject is a human. However, it must be noted that the study of adverse conditions of the central nervous system in non-human animals is only now beginning, and that some instances of such treatments are coming into use. For example, fluoxetine, and perhaps other serotonin reuptake inhibitors, are being used in companion animals such as dogs for the treatment of behavioral problems and the like. Accordingly, use of the present compounds in non-human animals is contemplated. It will be understood that the dosage ranges for other animals will necessarily be quite different from the doses administered to humans, and accordingly that the dosage ranges described below in the section on tobacco withdrawal must be recalculated. For example, a small dog may be only ¹/₁₀th of a typical human's size, and it will therefore be necessary for a much smaller dose to be used. The determination of an effective amount for a certain non-human animal is carried out in the same manner described below in the case of humans, and veterinarians are well accustomed to such determinations.

Further, the activity of compounds of Formula I in the inhibition of the reuptake of serotonin provides a method of inhibiting the reuptake of serotonin comprising administering to a subject in need of such treatment an effective amount of a compound of that formula. It is now known that numerous physiological and therapeutic benefits are obtained through the administration of drugs which inhibit the reuptake of serotonin. The treatment of depression with drugs of the class of which fluoxetine is the leader has become perhaps the greatest medical breakthrough of the past decade. Numerous other treatment methods carried out by the administration of the compounds of Formula I will be set out in detail below. Again, the effective amount of a compound for the inhibition of serotonin reuptake, or for a specific therapeutic method which depends on the inhibition of reuptake, is determined in the manner described below under the heading of smoking withdrawal.

Depression in its many variations has recently become much more visible to the general public than it has previously been. It is now recognized as an extremely damaging disorder, and one that afflicts a surprisingly large fraction of the human population. Suicide is the most extreme symptom of depression, but millions of people, not quite so drastically afflicted, live in misery and partial or complete uselessness, and afflict their families as well by their affliction. The introduction of fluoxetine was a breakthrough in the treatment of depression, and depressives are now much more likely to be diagnosed and treated than they were only a decade ago. Duloxetine is in clinical trials for the treatment of depression and is likely to become a marketed drug for the purpose.

Depression is often associated with other diseases and conditions, or caused by such other conditions. For example, it is associated with Parkinson's disease; with HIV; with Alzheimer's disease; and with abuse of anabolic steroids. Depression may also be associated with abuse of any substance, or may be associated with behavioral problems resulting from or occurring in combination with head injuries, mental retardation or stroke. Depression in all its variations is a preferred target of treatment with the present adjunctive therapy method and compositions.

Obsessive-compulsive disease appears in a great variety of degrees and symptoms, generally linked by the victim's uncontrollable urge to perform needless, ritualistic acts. Acts of acquiring, ordering, cleansing and the like, beyond any rational need or rationale, are the outward characteristic of the disease. A badly afflicted subject may be unable to do anything but carry out the rituals required by the disease. Fluoxetine is approved in the United States and other countries for the treatment of obsessive-compulsive disease and has been found to be effective.

Obesity is a frequent condition in the American population. It has been found that fluoxetine will enable an obese subject to lose weight, with the resulting benefit to the circulation and heart condition, as well as general well being and energy.

The present treatment methods are useful for treating many other diseases, disorders and conditions as well, as set out below. In many cases, the diseases to be mentioned here are classified in the International Classification of Diseases, 9th Edition (ICD), or in the Diagnostic and Statistical Manual of Mental Disorders, 3rd Version Revised, published by the American Psychiatric Association (DSM). In such cases, the ICD or DSM code numbers are supplied below for the convenience of the reader.

- depression, ICD 296.2 & 296.3, DSM 296, 294.80, 293.81, 293.82, 293.83, 310.10, 318.00, 317.00
- migraine
- pain, particularly neuropathic pain
- bulimia, ICD 307.51, DSM 307.51
- premenstrual syndrome or late luteal phase syndrome, DSM 307.90
- alcoholism, ICD 305.0, DSM 305.00 & 303.90
- tobacco abuse, ICD 305.1, DSM 305.10 & 292.00
- panic disorder, ICD 300.01, DSM 300.01 & 300.21
- anxiety, ICD 300.02, DSM 300.00
- post-traumatic syndrome, DSM 309.89
- memory loss, DSM 294.00
- dementia of aging, ICD 290
- social phobia, ICD 300.23, DSM 300.23
- attention deficit hyperactivity disorder, ICD 314.0
- disruptive behavior disorders, ICD 312
- impulse control disorders, ICD 312, DSM 312.39 & 312.34
- borderline personality disorder, ICD 301.83, DSM 301.83
- chronic fatigue syndrome
- premature ejaculation, DSM 302.75
- erectile difficulty, DSM 302.72
- anorexia nervosa, ICD 307.1, DSM 307.10
- disorders of sleep, ICD 307.4
- autism
- mutism
- trichotillomania While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., *REMINGTON'S PHARMACEUTICAL SCIENCES,* (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

FORMULATION EXAMPLE 1

Hard gelatin capsules containing the following ingredients are prepared:

| Ingredient | Quantity (mg/capsule) |
| --- | --- |
| Compound of Example 1 | 30.0 |
| Starch | 305.0 |
| Magnesium stearate | 5.0 |

The above ingredients are mixed and filled into hard gelatin capsules in 340 mg quantities.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:

1. A compound of Formula I

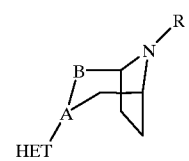

where

A-B is —C=CH—, or —CH—CH$_2$—;

R is H, or C$_1$–C$_4$; and

HET is a bicyclic heteroaryl group selected from indol-2-yl, indol-3-yl, benzothien-2-yl, benzothien-3-yl, benzofur-2-yl, benzofur-3-yl, benzothiazol-2-yl, benzoxazol-2-yl, quinolin-2-yl quinolin-3-yl, quinolin-4-yl, isoquinolin-1-yl, isoquinolin-3-yl, isoquinolin-4-yl, and quinoxalin-2-yl, each substituted on the phenyl ring with one or two substitutents independently selected from the group consisting of halo, C$_1$–C$_4$ alkyl, C$_3$–C$_6$ cycloalkyl, C$_1$–C$_4$ alkoxy, cyano, nitro, carboxamido, trifluoromethyl, or hydroxy; and pharmaceutically acceptable salts thereof.

2. A compound of claim 1 where A-B is —C=CH—.
3. A compound of claim 1 where A-B is —CH—CH$_2$—.
4. A compound of claim 1 where HET is indol-3-yl.
5. A compound of claim 2 where HET is indol-3-yl.
6. A compound of claim 3 where HET is indol-3-yl.
7. A method for the inhibition of serotonin reuptake in a mammal, comprising administering to a mammal in need of such treatment a serotonin reuptake inhibiting dose of a compound of Formula I

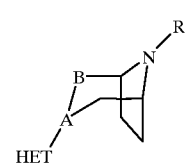

where

A-B is —C=CH—, or —CH—CH$_2$—;

R is H, or C$_1$–C$_4$; and

HET is a bicyclic heteroaryl group selected from indol-2-yl, indol-3-yl, benzothien-2-yl, benzothien-3-yl, benzofur-2-yl, benzofur-3-yl, benzothiazol-2-yl, benzoxazol-2-yl, quinolin-2-yl quinolin-3-yl, quinolin-4-yl, isoquinolin-1-yl, isoquinolin-3-yl, isoquinolin-4-yl, and quinoxalin-2-yl, each substituted on the phenyl ring with one or two substitutents independently selected from the group consisting of halo, C$_1$–C$_4$ alkyl, C$_3$–C$_6$ cycloalkyl, C$_1$–C$_4$ alkoxy, cyano, nitro, carboxamido, trifluoromethyl, or hydroxy; and pharmaceutically acceptable salts thereof.

8. A method of claim 7 where the mammal is a human.
9. A pharmaceutical formulation which comprises, in association with a pharmaceutically acceptable carrier, diluent or excipient, a compound of Formula I:

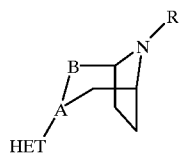

where
A-B is —C=CH—, or —CH—CH$_2$—;
R is H, or C$_1$–C$_4$; and

HET is a bicyclic heteroaryl group selected from indol-2-yl, indol-3-yl, benzothien-2-yl, benzothien-3-yl, benzofur-2-yl, benzofur-3-yl, benzothiazol-2-yl, benzoxazol-2-yl, quinolin-2-yl quinolin-3-yl, quinolin-4-yl, isoquinolin-1-yl, isoquinolin-3-yl, isoquinolin-4-yl, and quinoxalin-2-yl, each substituted on the phenyl ring with one or two substitutents independently selected from the group consisting of halo, C$_1$–C$_4$ alkyl, C$_3$–C$_6$ cycloalkyl, C$_1$–C$_4$ alkoxy, cyano, nitro, carboxamido, trifluoromethyl, or hydroxy; and pharmaceutically acceptable salts thereof.

* * * * *